United States Patent [19]

Leach et al.

[11] 4,258,220

[45] Mar. 24, 1981

[54] PURIFICATION OF 2,6-XYLENOL STREAMS

[75] Inventors: Bruce E. Leach; Charles M. Starks, both of Ponca City, Okla.

[73] Assignee: Conoco, Inc., Ponca City, Okla.

[21] Appl. No.: 116,057

[22] Filed: Jan. 28, 1980

[51] Int. Cl.$^3$ .................. C07C 37/68; C07C 37/11
[52] U.S. Cl. .................................. 568/804; 568/752
[58] Field of Search ................. 568/750, 804, 752

[56] References Cited

U.S. PATENT DOCUMENTS

| | | | |
|---|---|---|---|
| 2,435,087 | 1/1948 | Luten et al. | 568/750 |
| 2,448,942 | 9/1948 | Winkler et al. | 568/794 |
| 3,267,152 | 8/1966 | Hokama | 568/794 |
| 3,331,755 | 7/1967 | Neuworth | 568/752 |
| 3,446,856 | 5/1969 | Hamilton | 568/804 |
| 3,479,410 | 11/1969 | Hamilton | 568/804 |
| 3,642,912 | 2/1966 | Sharp et al. | 568/804 |
| 3,843,606 | 10/1974 | Sorge | 568/804 |
| 3,873,628 | 3/1975 | Sorge | 568/804 |
| 3,979,464 | 9/1976 | Leach | 568/804 |
| 3,996,297 | 12/1976 | Leach | 568/750 |

FOREIGN PATENT DOCUMENTS 857927 12/1970 Canada .................................. 568/804

Primary Examiner—Werren B. Lone
Attorney, Agent, or Firm—Cortlan R. Schupbach, Jr.

[57] ABSTRACT 2,6-xylenol admixed with meta,para-cresol is reacted with methanol in a contact with a titanium/SO$_4$/magnesium oxide catalyst to yield a product stream which can be readily distilled to give 2,6-xylenol in high purity. The particular catalyst used allows low loss of 2,6-xylenol during the reactions and low amounts of side products obtained.

8 Claims, No Drawings

PURIFICATION OF 2,6-XYLENOL STREAMS

This invention comprises an improved catalyst and method for the purification of 2,6-xylenol streams when in admixture with meta,para-cresol. More specifically, this invention relates to a process for purifying 2,6-xylenol from meta,para-cresol mixtures by methylating meta, para-cresols over magnesium oxide catalysts promoted by specific metal ions and sulfate ions.

Pure 2,6-xylenol is a desirable chemical intermediate in many chemical reactions and as such has a higher economic value than impure 2,6-xylenol. Normally the major impurity in 2,6-xylenol is a meta-cresol/para-cresol mixture (m,p-cresols). Separation by fractional distillation is difficult because the boiling points for 2,6-xylenol, meta-cresol and para-cresol are 201.0° C., 202.2° C. and 201.1° C. respectively. In the past, solvent extraction techniques have been used which involves dissolving a feed material containing from 5 to 12 weight percent of meta,para-cresol and toluene and contacting this feed material with approximately a 10% aqueous sodium hydroxide solution. The 2,6-xylenol in toluene phase is separated from the aqueous phase which contains the sodium salt in the meta,para-cresol. Acid is then added to the aqueous phase to recover the meta,para-cresol. The aqueous solution remaining contains some cresylic acid and is then treated prior to disposal. To complete the solvent extraction process, 2,6-xylenol is distilled from toluene. Cresylic acid is a mixture of phenolic compounds.

Canadian Pat. No. 857,927 shows a simplified method of using alumina catalyst to purify 2,6-xylenol in the vapor phase. However, this method, while effective, has a drawback in short catalyst life. U.S. Pat. No. 3,996,297 provided an improved method for carrying out such reactions over alumina in the liquid phase under controlled pressure conditions to provide longer catalyst life with separations in the range of about 78% recovery. However, all these processes are either expensive or produce large amounts of other by-products which must be disposed. It would be of great benefit to provide a process which removes the close boiling meta,para-cresols to large extent and does not convert significant amounts of desirable 2,6-xylenol to by-products. By-products produced should be valuable.

It is therefore an object of the present invention to provide a method of purifying 2,6-xylenol from contamination with meta-para-cresols. Other objects will become apparent to those skilled in this art as the description proceeds.

In accordance with the objects of the present invention there is provided a process for the purification of 2,6-xylenol from meta-para-cresol impurities. Concisely stated, the process comprises contacting a mixture of 2,6-xylenol and meta-para-cresols with from 0.1 to 5 mole ratios of a methylating agent, then passing over magnesium oxide catalyst promoted with specific metal sulfates at temperatures of from about 400° to about 500° C. under pressure conditions of from about atmospheric to about 5 atmospheres. The process is effective either in batch or continuous reaction. When carried out continuously a liquid hourly space velocity of from about 1 to about 15 can be used. The process is effective when used alone but can, of course, be used in combination with existing processes such as solvent extraction.

While temperatures of from about 400° to about 500° C. are practical, temperatures of from about 440° to about 465° C. are preferred. Pressures of from atmospheric to about 5 atmospheres are practical, but of course pressures of atmospheric to 2 atmospheres are most preferred for ease of operation. When carried out continuously, liquid hourly space velocities (LHSV) of from 0.5 to 15 can be used but LHSV from about 1.0 to 4 are preferred. A methanol mole ratio of from about 0.1 to about 5 can be used, but a mole ratio of from about 0.5 to about 1 is most preferred.

The basis of the present invention is converting meta-para-cresol to 2,4/2,5- and 2,3-xylenols. 2,4-/2,5- and 2,3-xylenols are easily separable from 2,6-xylenol by conventional fractional distillation methods. The 2,6-xylenol which has been purified can, of course, be recycled to further increase purity.

In carrying out the vapor phase methylation of the present invention, methanol is the preferred methylating agent. Other methylating agents can also be used. Examples of such methylating agents are alcohols such as ethanol and isopropanol and olefins such as propylene and isobutylene.

The catalysts of the present invention are magnesium oxide catalysts promoted with amorphous titanium, chromium and uranium in the presence of sulfate ion. Normally, the catalyst comprises from about 85 to about 90% by weight of magnesium oxide and 3 to 8% by weight amorphous titanium, chromium, uranium, or mixtures or these, and 1.5 to 8% by weight sulfate ion, all based on the total weight of the catalyst used. The ingredients of the catalyst can be varied within this range to suit the particular feed mixture being used.

In addition, it has been found useful but not critical to add to the catalyst from about 1 to about 4% by weight silica based upon the final weight of the catalyst. The function of the silica is not known other than it increases the effectiveness of the catalyst, possibly by increasing the surface area and longevity of the catalyst. Silica addition also greatly aids the crush strength of pellets formed from the catalyst. Of course, well known techniques of adding lubricating agents such as graphite in the amount of from about 1 to about 2% by weight of the final catalyst for pelletizing purposes can be used with the present catalyst. The graphite has no appreciable effect upon the methylation.

Likewise, it is desirable that the metal compounds of the present catalyst be in amorphous and not a crystalline form.

Magnesium oxide catalysts in general are known. U.S. Pat. No. 3,479,410 discloses vapor phase methylation of phenols over magnesium oxide by passing said phenols over the catalyst in the presence of 2,4,6-trimethylphenol. 2,4,6-trimethylphenol is necessary as an ingredient in the feedstream. Magnesium oxide which is specifically shaped by bonding with an inert organic polymeric binder as described in U.S. Pat. No. 3,843,606 and is used for the ortho alkylation of phenols. The inorganic binder is taught to be beneficial in extending catalyst life. However, this leaves one with the problem of regeneration of the magnesium oxide, since organic materials are degraded under regeneration conditions.

In U.S. Pat. No. 3,873,628, manganese sulfate is mixed with magnesium oxide resulting in a catalyst which is an ortho director when an alkyl alcohol is reacted with a phenolic compound. The combination is said to allow the alkylation to proceed at a lower temperature without reducing selectivity to the ortho position. However, the reaction produces sulfur dioxide as a by-product and must be removed before disposal in the atmosphere.

The catalysts of the instant invention do not deactivate as rapidly as many prior art catalysts under the reaction conditions of the instant invention. Catalyst life under these conditions exceeds 600 hours before deactivation becomes significant. Successive regenerations can be carried out without noticeable loss of catalyst activity are longevity.

Regeneration of the catalyst can be carried out by first cleaning the reactor containing the deactivated catalyst with steam. Air mixed with steam is introduced into the reactor. The amount of air is controlled to maintain temperature in the reactor at about 500° C. Air content is gradually increased until no exotherm is observed. The reactor is then purged with steam or an inert gas before restarting the reaction.

The instant invention is more concretely described with reference to the examples below wherein all parts and percentages are by weight unless otherwise specified. Examples are provided to illustrate the present invention and not to limit it.

In the examples below, a titanium$^{+4}$/SO$_4$$^{-2}$/magnesium oxide catalyst was used.

The catalysts of the present invention are formed using special preparation. In general, the catalysts are prepared by dissolving metal sulfate in water, then adding to the magnesium oxide catalyst. The solution is evaporated to dryness and calcined in air for 2 hours at about 500° C.

In the specific examples set forth, 2.8 grams of titanium sulfate was dissolved in about 12 cubic centimeters of water. The solution was added to 25 grams of magnesium oxide catalyst (Harshaw Mg-0601) trademark of and sold by Harshaw Chemical Company. The solution was evaporated to dryness and calcined in air for 2 hours at about 500° C.

EXAMPLE 1

The reaction was carried out at a temperature of 455° C., an LHSV of 2.0 and a methanol/phenolic ratio of 0.5. An impure 2-xylenol feed having 2.1% ortho cresol, 8.7% meta-para-cresol and 89.2% 2,6-xylenol was used. Nine weight percent water was added to the feed to extend catalyst life. The reaction was carried out continuously and the product was analyzed by gas liquid chromatography (GLC). The weight percents of products were determined by a computerized program calculating the area under the various curves. The results of the experiments are set forth in Table 1.

TABLE 1

| Component | Wt. Percent |
| --- | --- |
| phenol | 0.12 |
| o-cresol | 3.75 |
| m,p-cresol | |
| 2,6-dimethylanisole) | 1.47 |
| 2,6-xylenol | 81.69 |
| 2,4-/2,5-xylenol | 3.89 |
| 2,3-xylenol | 0.53 |
| 2,4,6-trimethylphenol | 6.03 |
| 2,3,6-trimethylphenol | 2.22 |
| other trimethylphenols | 0.11 |
| tetramethylphenol | 0.19 |
| | 100.00 |

An analysis of the results of the table show that the 2,6-xylenol recovery was 91.6% of the original contained in the feed. This compares to an average of 78.4% recovery by the two known alternate processes using alumina as set forth in Canadian Pat. No. 857,927 and U.S. Pat. No. 3,996,297. When meta-para-cresol is above two weight percent in the product, 2,6-xylenol is recovered in less than 99% purity.

The remaining weight percentage products are all directed toward 2,3,6-trimethylphenol, 2,4,6-trimethylphenol, and 2,3,4,6-/2,3,5,6-tetramethylphenols. It can be clearly seen from the data that a promoted magnesium oxide catalyst of the present invention are much more effective on a percentage product basis than the previous reactions carried out over alumina catalysts.

EXAMPLE 2

A reaction was carried out using a catalyst containing no silica. The catalyst was prepared by adding 5.4 g of ground MgSO$_4$ to 77.8 g MgO powder (Merck Maglite D). Titanium isopropoxide (6.5 g) was diluted with an equal weight of isopropanol and the resulting liquid mixture added to the powder mixture. The liquid and powder were well mixed. Water (50 cc) was added to the mixture, which was then dried, sifted through a 60 standard mesh screen, and tableted. The tablets were dried overnight at 150° C., then calcined 2 hours at 500° C. prior to use. The tablets were more easily crushed than similar tablets formed using silica.

A reaction was carried out with a feed containing 6 weight percent methanol and 5 weight percent water at atmospheric pressure, 458° C. and an LHSV of 2.0. The example is summarized in Table 2. Of the original 2,6-xylenol in the feed, 93 percent was unreacted.

TABLE 2

| Component | Feed w/o | Product w/o |
| --- | --- | --- |
| o-cresol | 1.85 | 2.02 |
| m,p-cresol | 6.25 | 0.21 |
| 2,6-xylenol | 91.90 | 85.48 |
| 2,4/2,5-xylenol | | 1.53 |
| 2,3-xylenol | | 0.22 |
| 2,4,6-trimethylphenol | | 6.43 |
| 2,3,6-trimethylphenol | | 3.62 |
| higher boiling methylphenols | | 0.49 |
| | | 100.00 |

While certain embodiments and details have been shown for the purpose of illustrating this invention, it will be apparent to those skilled in this art that various changes and modifications may be made herein without departing from the spirit and scope of the invention.

We claim:

1. An improved method for separating 2,6-xylenol from admixture with meta-para-cresols by methylating meta-para-cresols with methanol over a catalyst to form 2,4-/2,5-xylenol and 2,3-xylenol, then separating 2,6-xylenol from the product mixture by distillation, wherein the methylation is carried out at temperatures of from about 400° C. to about 500° C., pressures of from about atmospheric to about 10 atmospheres and a methanol/phenolic mole ratio of from about 0.1 to about 5.0, the improvement comprising using a catalyst comprising
   (a) about 85 to about 90% by weight magnesium oxide,
   (b) 3 to 8% by weight amorphous titanium, chromium, uranium, or mixtures of these,
   (c) 1.5 to 8% by weight sulfate ion, all based on the total weight of the catalyst.

2. A method as described in claim 1 wherein 3 to 8% by weight amorphous titanium or chromium or mixtures of these is used.

3. A method as described in claim 2 wherein the methylation is carried out continuously.

4. A method as described in claim 3 wherein the LHSV is from about 0.5 to about 10.0.

5. A method as described in claim 4 wherein the catalyst in addition contains from about 1.0 to about 4.0% by weight silica.

6. A method as described in claim 5 wherein the catalyst contains in addition from about 1 to about 2% by weight graphite pelletizing lubricant.

7. A method as described in claim 6 wherein the catalyst is formed with amorphous titanium.

8. An improved method for separating 2,6-xylenol from admixture with meta-para-cresols by methylating meta-para-cresols with alkylating agents selected from the group consisting of ethanol, isopropanol, propylene, and isobutylene over a catalyst to form 2,4-/2,5-xylenol and 2,3-xylenol, then separating 2,6-xylenol from the product mixture by distillation, wherein the methylation is carried out at temperatures of from about 400° C. to about 500° C., pressures of from about atmospheric to about 10 atmospheres and an alkylation agent phenolic mole ratio of from about 0.1 to about 5.0, the improvement comprising using a catalyst comprising (a) about 85 to about 90% by weight magnesium oxide,
(b) 3 to 8% by weight amorphous titanium, chromium, uranium, or mixtures of these,
(c) 1.5 to 8% by weight sulfate ion, all based on the total weight of the catalyst.

* * * * *